United States Patent [19]
Franz et al.

[11] 3,971,648
[45] July 27, 1976

[54] HERBICIDAL USE OF CARBOXYALKYL ESTER OF N-PHOSPHONOMETHYL GLYCINE

[75] Inventors: John E. Franz, Crestwood; Hans L. Nufer, Creve Coeur, both of Mo.

[73] Assignee: Monsanto Company, St. Louis, Mo.

[22] Filed: Sept. 16, 1974

[21] Appl. No.: 506,139

Related U.S. Application Data

[62] Division of Ser. No. 417,858, Nov. 21, 1973, Pat. No. 3,868,407.

[52] U.S. Cl. .................................................. 71/86
[51] Int. Cl.$^2$ ......................................... D01N 9/36
[58] Field of Search ...................................... 71/86

[56] References Cited
UNITED STATES PATENTS
3,799,758   3/1974   Franz ..................................... 71/86

*Primary Examiner*—Lewis Gotts
*Assistant Examiner*—Catherine L. Mills
*Attorney, Agent, or Firm*—William T. Black; Donald W. Peterson

[57] ABSTRACT

Carboxyalkyl esters of N-phosphonomethyl glycine and their salts and a process for their preparation are described. These esters and salts are useful as contact herbicides.

7 Claims, No Drawings

HERBICIDAL USE OF CARBOXYALKYL ESTER OF N-PHOSPHONOMETHYL GLYCINE

This is a division of application Ser. No. 417,858, filed Nov. 21, 1973, now U.S. Pat. No. 3,868,407.

This invention relates to novel carboxyalkyl esters of N-phosphonomethyl glycine and the salts thereof and herbicidal compositions and methods.

The novel carboxyalkyl esters of the present invention have the formula

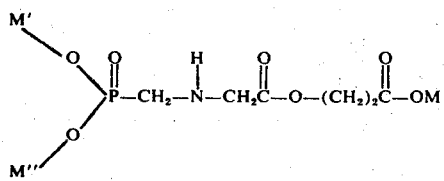

wherein M, M' and M'' are independently selected from the group consisting of hydrogen, alkali metals, alkaline earth metal, ammonium, and organic ammonium groups.

A preferred embodiment of this invention are those compounds wherein at least one of M, M' and M'' is hydrogen, alkali metal, alkaline earth metal, ammonium or organic ammonium.

The novel carboxyalkyl esters of this invention are prepared by the reaction of N-phosphonomethyl glycine in a water solution with a lactone such as propiolactone in the presence of a base and then neutralization of the base with hydrochloric acid. The various salts are prepared by treating the free acid with an appropriate base.

The temperature of the reaction is normally maintained at about 20°C., although higher or lower temperatures are possible.

The order of addition of the reactants is critical. It is essential to add the lactone to a basic water solution of N-phosphonomethyl glycine. For convenience and ease of isolation of the product, the carboxyalkyl ester, it is preferred to employ equal molar amounts of the lactone and N-phosphonomethyl glycine.

The reaction is normally conducted at atmospheric pressure although super-atmospheric and sub-atmospheric pressures may be employed.

The term "alkali-metal" encompasses lithium, sodium, potassium, cesium and rubidium; and the term "alkaline earth metal" includes beryllium, magnesium, calcium, strontium and barium.

The organic ammonium salts included in the above formula are those prepared from low molecular weight organic amines, i.e. having a molecular weight below about 300, and such organic amines include the alkyl amines, alkylene amines and alkanol amines containing not more than 2 amine groups, such as methylamine, ethylamine, n-propylamine, isopropylamine, n-butylamine, isobutylamine, sec-butylamine, n-amylamine, isoamylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, di-heptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine and propylenediamine.

The following examples serve to further illustrate the invention. In the examples, all parts and percents are by weight unless otherwise expressly set forth.

EXAMPLE 1

Into a 500 ml. round bottomed flask was charged N-phosphonomethyl glycine (17 g.), water (200 ml.) and sodium hydroxide (12 g.) and the mixture stirred until a clear solution was obtained. The solution was cooled to 20°C. and propiolactone (8 g.) was added over a 15 minute period with stirring. The stirring was continued for 1 hour at room temperature. The reaction mixture was acidified with hydrochloric acid during which time a solid formed to give an aqueous slurry. The solid was removed by filtration and dried. The solid was identified as 2-carboxyethyl-N-phosphonomethyl glycinate (Compound I), (m.p. 211°C. with decomposition) and gave the following elemental analysis:

|   | CALCULATED | FOUND |
|---|---|---|
| C | 29.79% | 29.78% |
| H | 5.33% | 5.08% |
| N | 5.79% | 5.71% |
| P | 12.80% | 12.63% |

EXAMPLE 2

A water solution of the bis(isopropylamine)salt of 2-carboxyethyl-N-phosphonomethyl glycinate was prepared as follows:

2-Carboxyethyl-N-phosphonomethyl glycinate (4.04 g.) was slurried in water (5.0 g.). To the mixture, with cooling, was added isopropylamine (1.92 g.) was added, yielding a water solution containing the bis(isopropylamine)salt of 2-carboxyethyl-N-phosphonomethyl glycinate (Compound II).

EXAMPLE 3

A water solution of glycine, 2-carboxyethylester-N-(disodium phosphonomethyl) was prepared as follows.

2-Carboxyethyl-N-phosphonomethyl glycinate (4.04 g.) was slurried in water (5.28 g.). To the mixture, with cooling, was added sodium hydroxide (1.36 g.) to yield a water solution containing the disodium salt of N-(disodium phosphonomethyl), (Compound III).

By following the procedure of Examples 2 and 3 and employing the proper base or ammonium compound, a ratio of 1 or 2 equivalents of base for each equivalent of the 2-carboxyethyl-N-phosphonomethyl glycinate, the following salts can be prepared:

Monobutylamine salt of 2-carboxyethyl-N-phosphonomethylglycinate

Mono-(trimethylamine) salt of 2-carboxyethyl-N-phosphonomethylglycinate
Mono(diethylenetriamine) salt of 2-carboxyethyl-N-phosphonomethylglycinate
Monoisopropylamine salt of 2-carboxyethyl-N-phosphonomethylglycinate
Mono-n-propylamine salt of 2-carboxyethyl-N-phosphonomethylglycinate
Mono(dipropargylamine) salt of 2-carboxyethyl-N-phosphonomethylglycinate
Monosodium salt of 2-carboxyethyl-N-phosphonomethylglycinate
Potassium salt of 2-carboxyethyl-N-phosphonomethylglycinate pO Mono(dialkylamine) salt of 2-carboxyethyl-N-phosphonomethylglycinate
Monolithium salt of 2-carboxyethyl-N-phosphonomethylglycinate
Trisodium salt of 2-carboxyethyl-N-phosphonomethylglycinate
Monocesium salt of 2-carboxyethyl-N-phosphonomethylglycinate
Dipotassium salt of 2-carboxyethyl-N-phosphonomethylglycinate
Tripotassium salt of 2-carboxyethyl-N-phosphonomethylglycinate
Monocyclohexylamine salt of 2-carboxyethyl-N-phosphonomethylglycinate
Di(methylamine) salt of 2-carboxyethyl-N-phosphonomethylglycinate
Di(dimethylamine) salt of 2-carboxyethyl-N-phosphonomethylglycinate
Di(ethylamine) salt of 2-carboxyethyl-N-phosphonomethylglycinate
Di(n-propylamine) salt of 2-carboxyethyl-N-phosphonomethylglycinate
Di(iso-butylamine) salt of 2-carboxyethyl-N-phosphonomethyl glycinate
Mono(oleylamine) salt of 2-carboxyethyl-N-phosphonemethylglycinate
Mono(steaylamine) salt of 2-carboxyethyl-N-phosphonomethylglycinate
Mono(tallowamine) salt of 2-carboxyethyl-N-phosphonomethylglycinate
Mono(methylbutylamine) salt of 2-carboxyethyl-N-phosphonomethylglycinate

EXAMPLE 4

The post-emergent herbicidal activity of the compounds of this invention is demonstrated as follows. The active ingredients are applied in spray form to 14 or 21 day old specimens of the various plant species. The spray, a water solution containing the active ingredient and a surfactant (35 parts butylamine salt of dodecylbenzene sulfonic acid and 65 parts tall oil condensed with ethylene oxide in the ratio of 11 moles ethylene oxide to 1 mole tall oil) is applied to the plants in different sets of pans at several rates (pounds of active ingredient per acre). The treated plants are placed in a greenhouse and the effects are observed and recorded after approximately 2 weeks or approximately 4 weeks as is indicated in the table.

The post-emergence herbicidal index used in the table is as follows:

| PLANT RESPONSE | INDEX |
|---|---|
| No Injury | 0 |
| Slight Injury | 1 |
| Moderate Injury | 2 |
| Severe Injury | 3 |
| Killed | 4 |

TABLE I

| Compound | Rate lb/acre | Canada Thistle | Cocklebur | Velvetleaf | Morningglory | Lambsquarters | Smartweed | Nutsedge | Quackgrass | Johnsongrass | Bromus Tectorum | Barnyard Grass | Observed Weeks After Treatment |
|---|---|---|---|---|---|---|---|---|---|---|---|---|---|
| I | 4 | — | 1 | 0 | 1 | 3 | 0 | 0 | 1 | 0 | 0 | 3 | 2 |
|  |  | — | 1 | 0 | 1 | 3 | 0 | 0 | 1 | 0 | 1 | 3 | 4 |
| II | 10 | 3 | 3 | 2 | 2 | 3 | — | 1 | 1 | 2 | 2 | 2 | 2 |
|  |  | 3 | 3 | 3 | 3 | 3 | — | 2 | 2 | 2 | 3 | 3 | 4 |
|  | 4 | 1 | 1 | 1 | 2 | 3 | 2 | 0 | 0 | 1 | 0 | 1 | 2 |
|  |  | 1 | 1 | 1 | 2 | 4 | 2 | 0 | 0 | 0 | 0 | 2 | 4 |
| III | 10 | 2 | 2 | 2 | 2 | 2 | 0 | 2 | 0 | 2 | 2 | 3 | 2 |
|  |  | 3 | 2 | 2 | 2 | 3 | 0 | 2 | 1 | 3 | 3 | 3 | 4 |
|  | 4 | 2 | 1 | 2 | 2 | 2 | 1 | 0 | 0 | 1 | 1 | 2 | 2 |
|  |  | 2 | 1 | 2 | 2 | 2 | 2 | 0 | 1 | 1 | 1 | 3 | 4 |

For the sake of brevity and simplicity, the term "active ingredient" is employed hereinafter in this specification to describe the carboxyalkyl ester of N-phosphonomethyl glycine derivatives of this invention, hereinbefore described.

In herbicidal compositions, the active ingredient can be admixed with one or more adjuvants which can be solid or liquid extenders, carriers, diluents, conditioning agents and the like. The herbicidal formulations comprise wettable powders, aqueous suspensions, dust formulations, emulsifiable oils and solutions in solvents. In general, these formulations can all contain one or more surface-active agents.

Surface-active agents which can be used in herbicidal formulations are well known to those skilled in the art and have been well documented in U.S. Patents, bulletins and textbooks.

The preparation formulations and particle size of the wettable powders, aqueous suspensions, dusts, emulsifiable oils and solutions in solvents are also well known to those skilled in the art and well documented.

The active ingredient is usually present in the herbicidal compositions in a range of about 0.5 to 95 parts by weight per 100 parts by weight of wettable powder and dust formulations; 5 to 95 parts by weight per 100 parts by weight emulsifiable oil formulations. Formulations containing other than the above quantities of active ingredient can easily be prepared by those skilled in the art.

Application of the herbicidal compositions of this invention to the plant is well-known to those skilled in the art. The application of liquid and particulate solid herbicidal formulations to the above-ground portions of plants can be carried out by conventional methods, e.g., power dusters, boom and hand sprayers and spray dusters.

The active ingredient can be admixed with 1 or more adjuvants which can be solid or liquid extenders, carriers, diluents, conditioning agents and the like to form herbicidal compositions. Herbicidal formulations contain the active ingredients of this invention with wettable powders, aqueous suspensions, dust formulations, emulsifiable oils and solutions in solvents. In general, these formulations can all contain one or more surface-active agents. Herbicidal mixtures are applied at a rate of 1 to 50 parts per acre of active ingredient for general herbicidal effect.

While the illustrative embodiments of the invention have been described hereinbefore with particularity, it will be understood that various other modifications will be apparent to and can readily be made by those skilled in the art without departing from the scope and spirit of the invention. According, it is not intended that the scope of the claims appended hereto be limited to the examples and description set forth herein but rather the claims be construed as encompassing all the features of patentable novelty which reside in the present invention including all features which would be treated as equivalents thereof by those skilled in the art to which the invention pertains.

What is claimed is:

1. The herbicidal method which comprises contacting a plant with a herbicidally effective amount of a compound of the formula

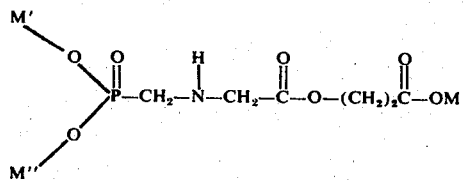

wherein M is hydrogen, alkali metal, alkaline earth metal, ammonium or organic ammonium, M' and M'' are hydrogen, alkali metal, alkaline earth metal, ammonium or organic ammonium, said organic ammonium group being derived from an organic amine having a molecular weight below about 300 and containing not more than two amine groups.

2. The herbicidal method of claim 1 wherein the compound is β-carboxyethyl-N-phosphonomethyl glycinate.

3. The herbicidal method of claim 1 wherein the compound is the monoisopropylamine salt of β-carboxyethyl-N-phosphonomethyl glycinate.

4. A herbicidal composition comprising a herbicidally effective amount of a compound of the formula

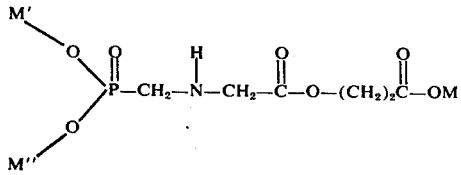

wherein M is hydrogen, alkali metal, alkaline earth metal, ammonium or organic ammonium, M' and M'' are hydrogen, alkali metal, alkaline earth metal, ammonium or organic ammonium, said organic ammonium group being derived from an organic amine having a molecular weight below about 300 and containing not more than two amine groups, and an adjuvant.

5. A herbicidal composition of claim 4 which also contains a surface-active agent.

6. A herbicidal composition of claim 4 wherein the compound is β-carboxyethyl-N-phosphonomethyl glycinate.

7. A herbicidal composition of claim 4 wherein the compound is monoisopropylamine alt of β-carboxyethyl-N-phosphonomethyl glycinate.

* * * * *